United States Patent [19]

Hansen et al.

[11] Patent Number: 4,997,646

[45] Date of Patent: Mar. 5, 1991

[54] USE OF INTERFERONS OF THE ALPHA FAMILY TO ENHANCE FERTILITY IN MAMMALS

[75] Inventors: Peter J. Hansen, Gainesville, Fla.; Kazuhiko Imakawa; R. Michael Roberts, both of Columbia,, Mo.; William W. Thatcher, Gainesville, Fla.

[73] Assignees: University of Florida Research Foundation, Inc., Alachua, Fla.; Currators of the University of Missouri, Columbia, Mo.

[21] Appl. No.: 312,853

[22] Filed: Feb. 23, 1989

[51] Int. Cl.$^5$ ............................................... A61K 37/66
[52] U.S. Cl. ................................... 424/85.7; 424/85.4
[58] Field of Search ............................... 424/85.4, 85.7

[56] References Cited

PUBLICATIONS

Charpigny et al., Febs Letters, vol. 228, No. 1, pp. 12-16, Feb. 1988.
Pontzer et al., Biochem. Biophys. Res. Comm., vol. 152, No. 2, 1988, pp. 801-807.
Plante et al., Endocrinology, vol. 122, No. 5, May 1988, pp. 2342-2344.
Bazer et al., J. Animl. Sci, 57, suppl. p. 425 (1983).
Godkin et al., 54, J. Reprod. Fertil, p. 141 (1982).
Godkin et al., 114, Endocrinology, p. 120 (1984).
Godkin et al., J. Reprod. Fertil, 71, p. 57 (1984).
Helmer et al., J. Reprod. Fertil, 79, p. 83 (1987).
Hansen et al., Endocrinology, 117, p. 1424 (1985).
Imikawa et al., Nature, 330, p. 377 (1987).
Martal et al., J. Reprod. Fertil., 56, p. 63 (1979).
Rowson et al., J. Reprod. Fertil., 13, p. 511 (1967).
Stewart et al., J. Endocrinology, 115, p. R 13-R 15 (1987).
Knickerbocker et al., J. Reprod. Fertil, 77, p. 381 (1986).
Bradford, Anal Biochem, 72, p. 248 (1976).
Familletti et al., Methods Enzymol., 78, p. 387 (1981).
Anthony et al., Endocrinology, 123, p. 1274 (1988).
Helmer et al., Mol. Cell Endocrinology, 58, p. 103, (1988).
Thatcher et al., J. Reprod. Fertil., Suppl. 37, pp. 91-99 (1987).

Primary Examiner—Margaret Moskowitz
Assistant Examiner—Choon Koh
Attorney, Agent, or Firm—Mathews, Woodbridge & Collins

[57] ABSTRACT

A method for enhancing the fertility and for prolonging the lifespan of the corpus luteum in female mammals. The method comprising administering to the female mammal an effective amount of an interferon alpha together with one or more pharmaceutically acceptable excipients.

46 Claims, 3 Drawing Sheets

USE OF INTERFERONS OF THE ALPHA FAMILY TO ENHANCE FERTILITY IN MAMMALS This is a continuation-in-part of application Ser. No. 07/164,034, filed Mar. 4, 1988, now abandoned.

FIELD OF THE INVENTION

The present invention is directed to the field of animal and human health, and more particularly, to a method of use of interferons alpha (IFNα) to enhance fertility in mammals and to prolong the lifespan of the corpus luteum. The method of the present invention prevents early embryonic losses and increases the efficiency of reproduction in mammals.

BACKGROUND OF THE INVENTION

In mammals the corpus luteum (CL) of the ovary secretes progesterone, the hormone that maintains the uterus in a state adequate for pregnancy. The requirement for a fully functional CL may continue throughout pregnancy, as in the pig and cow, or end before term, as in the ewe, where the placenta and/or adrenal glands may assume the production of progesterone after 50 days of pregnancy (BAZER and FIRST, 1983). The demise of the corpus luteum, through a process called luteolysis, is mediated by uterine secretion of prostaglandin $F_2\alpha$ ($PGF_2\alpha$). It ensures termination of pregnancy.

The conceptus within the uterus is believed to produce a substance or substances which directly or indirectly prolong the lifespan of the corpus luteum and prevent a return to ovarian cyclicity. This phenomenon is known as 'maternal recognition of pregnancy' (SHORT, 1969). These substances are proteins referred to as trophoblast antiluteolysin, trophoblastin or trophoblast protein-1 (ROWSON and MOOR 1967, MARTAL et al 1979, BAZER et al 1986).

Ovine trophoblast protein-1 (oTP-1) is the major secretory product synthesized by the sheep conceptus between day 13 and 21 of pregnancy (GODKIN et al 1982). The protein consists of 3-4 isoelectric variants (with isoelectric points between 5.5 and 5.8) with a relative molecular weight of 17,000 to 21,000 (HANSEN et al 1985). Infusion of oTP-1 into the uterine lumen of non-pregnant ewes prevents CL regression and extends the estrous cycle (GODKIN et al 1984). The mechanism of action is not fully understood but oTP-1 has been shown to act on the uterine endometrium, altering protein secretion and phospholipid metabolism (GODKIN, BAZER and ROBERTS 1984). Such an effect would tend to reduce prostaglandin $F_2\alpha$ synthesis.

The cow conceptus secretes related molecules that cross react with antiserum to oTP-1. They are secreted by the cow conceptus between day 15-25 of pregnancy. The family of molecules is called bovine trophoblast protein-1 (bTP-1) and includes two structurally related glycoproteins of 22,000 and 24,000 molecular weight, each of which is present in three isoforms that arise from different messages (HELMER et al. 1987; ANTHONY et al., 1988; HELMER et al., 1988).

Recently a cDNA for oTP-1 has been sequenced (IMAKAWA et al 1987). Its primary amino-acid sequence inferred from the nucleotide sequence has 45-55% homology with a range of human, bovine, mouse, rat and pig interferons of the alpha family. Similarly, cDNA clones of the bovine trophoblast proteins (bTP-1) have been obtained and sequenced (Roberts and Imakawa, unpublished information). The sequences of mature oTP-1 and bTP-1 are each 172 amino acids in length. bTP-1 is 79.7% identical with oTP-1 within the region of the mature protein. oTP-1 is 70.3% homologous in sequence with rbINFα$_{II}$, whereas bTP-1 is only 69.2% homologous. The signal sequences for bTP-1 and oTP-1 differ in one residue out of 23. The signal sequences of bTP-1 and rBoIFNα$_{II}$ are identical. Preliminary observations suggest that different isolates of oTP-1 and bTP-1 are closely related and differ in sequence by few amino acids (Roberts and Imakawa, unpublished observations). It appears therefore that trophoblast proteins represent a group of proteins with high sequence conversation. This is in contrast to the interferons alpha derived from leukocytes which have been shown to differ widely in structure in all species tested.

Interferons have generally been named after the species of animal producing them (for example, human, ovine, bovine, murine, etc.), the type of cell involved in their production (for example, leukocyte, lymphoblastoid, fibroblast) and, occasionally, the type of the agent inducing their production (for example, virus, immune). A further classification refers to Type I or Type II comprehending virus and nucleic acid induced interferons. A recent classification refers to alpha, beta and gamma which correspond to previous designations of leukocyte, fibroblast, and type II (immune) interferons, respectively. The interferon employed herein is identified simply by animal species and the cell type producing it (for example, bovine interferon alpha).

The preparation of mammalian interferons of the alpha family is described in the art. The isolation of mammalian IFNα and/or the preparation thereof by means of recombinant DNA technology is described, for example, in the following patents and patent applications: U.S. Pat. Nos. 4,273,703; 4,328,207; EP-002,375; U.S. Pat. Nos. 4,262,090; 4,530,901; 4,414,150; EP-0,088,622; JP-58/224,690; U.S. Pat. Nos. 4,582,800 and 3,951,740. Interferons useful in accordance with the present invention are not limited to those alpha interferons described in the above cited literature. Further useful alpha interferons are known in the art.

Throughout the present specification an interferon of the alpha family (IFN α) is understood to represent a leukocyte-derived interferon or an interferon produced by means of recombinant DNA technology which still has the structural, immunological and antiviral and other biological properties of a leukocyte-derived interferon.

In contrast thereto, the trophoblast proteins (antiluteolytic proteins), e.g. oTP-1 and bTP-1, are conceptus—derived proteins. Despite certain homologies referred to above the relationship between trophoblast proteins and interferons is not yet fully clarified. It has been shown that with respect to in-vitro actions on endometrial protein and prostaglandin metabolism, actions of bTP-1 differ markedly from those of IFN-α (Thatcher et al., 1988).

It is an objective of the present invention to provide a method for enhancing fertility in female mammals and to prolong the lifespan of mammalian corpus luteum.

These and other objectives will be apparent from the following description of the invention.

DETAILED DESCRIPTION OF THE INVENTION

Figure 1:
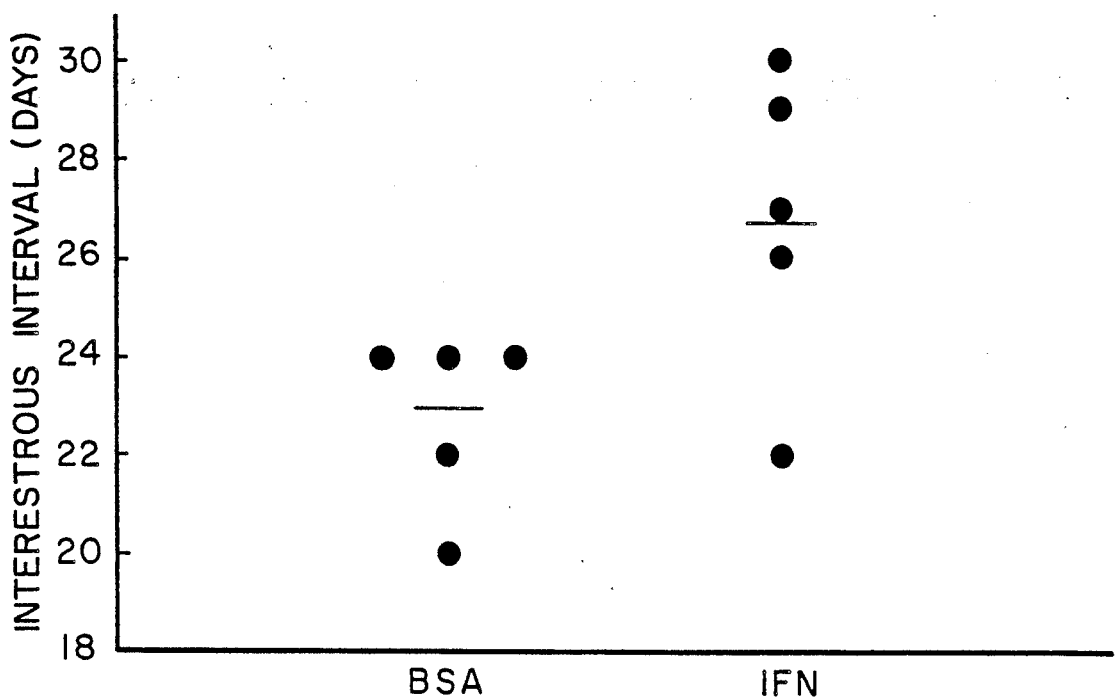
FIG. 1 shows the effect of intrauterine administration of bovine serum albumin (BSA) and interferon (IFN) solutions into the uterus of cyclic cows from Day 15.5 to 21 after estrus, on the interestrous interval. BSA administration was given as a control for IFN. Circles represent data for individual animals and horizontal lines represent average interestrous intervals. The mean interestrous interval was greater ($P<0.02$) for IFN-treated cows ($26.8 \pm 1.39$ d) than for BSA-treated cows ($22.8 \pm 0.80$ d).

Surprisingly, it has been found that in mammals the lifespan of the corpus luteum can be prolonged and fertility can significantly be enhanced by administering to a mammal an effective amount of an interferon of the alpha family (IFN$\alpha$). This is the more surprising because the interferons are proteins produced by totally different cells than the secretory trophoblast proteins. They have different actions on endometrium than the trophoblast proteins, and one could not predict from the prior art at the time this invention was made that interferons alpha when administered to a mammal would increase mammalian fertility or would have any effect to the corpus luteum.

Accordingly, one objective of the present invention is a method for enhancing fertility in a female mammal (animal or human, preferably animal) comprising administering to said mammal an effective mammalian fertility enhancing amount of an interferon alpha together with one or more pharmaceutically acceptable adjuncts, or excipients.

A further objective is a method of prolonging the lifespan of the corpus luteum in a mammal (animal or human, preferably animal) comprising administering to said mammal an effective corpus luteum lifespan prolonging amount of an interferon alpha together with one or more pharmaceutically acceptable adjuncts or excipients.

Both methods are applicable to healthy mammals with normal fertility to increase their fertility, to mammals with reduced fertility to return it to an acceptable level or to mammals which are difficult to settle.

It is understood that the expression 'mammal' includes but is not limited to primates (such as humans and monkeys), to domestic and wild animals, (for example, to farm animals such as cattle, horses, donkeys, deer, sheep, goats and pigs), to pets (such as dogs, cats and hamsters), and to fur bearing animals (such as minks, nutrias and ocelots).

A preferred target group of animals consists of cattle, sheep, goats and pigs.

The interferon useful in accordance with the present invention is a human or an animal interferon of the alpha family which is either isolated from mammalian leukocyte cells or which is produced by means of recombinant DNA technology still showing the immunological and antiviral and other biological properties of a leukocyte-derived interferon. This interferon may be of the alpha II or alpha I type. IFN$\alpha_I$ and IFN$\alpha_{II}$ represent preferred embodiments of the present invention. The interferon is further of homologous or heterologous origin with respect to the mammal to be treated. The interferon of homologous origin is preferred. Preferred animal interferons are bovine, ovine and porcine interferons alpha, more preferred is bovine interferon alpha, especially bovine interferon alphaI and alphaII. Most preferred is rbovine interferon alpha$_I$1 (rBoIFN$\alpha_I$1). The human and animal interferons are either of the alpha I or the alpha II type.

The amount of interferon administered to the mammal is an effective mammalian fertility enhancing amount or an effective corpus luteum lifespan prolonging amount. The lower limit is a daily dose of 0.1 mg/mammal, preferably 0.5 mg/mammal. The upper limit is the largest dose tolerated by the mammal without serious side effects. When given parenterally, the upper limit is, for example, about 100 mg/mammal per day, preferably 50 mg/mammal per day. When administered into the uterus, the lower limit is a daily dose of 0.1 mg/mammal, preferably 0.5 mg/mammal. The upper limit is, for example, about 25 mg/mammal per day, preferably 10 mg/mammal per day, more preferably 5 mg/mammal per day.

The interferon is administered in form of a single dose per day, in smaller portions or permanantly, for example, in form of a slow release formulation including implants. The interferon is most effective when administered to a fully developed female mammal at the time of maternal recognition of pregnancy or, in other words, in mammals in possession of a functioning corpus luteum. Farm animals normally are dosed between day 12 and 26 postestrous and insemination.

The dose may vary from one genus of animal to the other and may even vary within the same genus since said dose depends, inter alia, on the weight, the age and constitution of the animal but can easily be determined by a person skilled in the art.

Interferon is usually stored in its lyophilized (freeze-dried) form. For use in the present invention, the lyophilized interferon may be reconstituted in a pharmaceutical acceptable diluent (ready to use solution), preferably in sterile water, for injection (USP) or with pharmaceutical acceptable solid carriers. The aqueous solution is generally applicable, but the formulation can also be adapted to the specific type of administration. The interferon is administered orally, parenterally, percutaneously, intravaginally, by implant or in utero through the cervix.

Oral administration may be performed by mixing the interferon in food or drinking water, vitamin or mineral supplement, or by administering oral dosage forms such as drenches (animals), tablets, bolus, or capsules. Such oral means of administration are well known in the art.

Parenteral administration may be conveniently accomplished by, for example, subcutaneous, intradermal, intramuscular, and even intraveneous injection. Parenteral administration is well known in the art and may be carried out in ways usual in the animal veterinary or human medical art.

A method to achieve prolonged release (so called 'slow release') could be the use, parenterally, intravaginally or in utero, of oil solutions/oil suspensions of the interferon. Including gelling agents like aluminum monostearate, or carbohydrates (cellulose, pectin, dextran derivatives), polysiloxanes or proteins (gelatin, collagen) could further extend the releasing time of the Interferon after parenteral, intravaginal or intra-uterine application. Furthermore, implants made from silicone or wax, or other implantable matrices from polymeric materials can be used subcutaneously to deliver the Interferon over the required period of time.

Polysiloxane carriers are described in the art for a variety of hormonal delivery forms and can be adapted to the release of interferons. The intravaginal administration includes the use of collagen sponges with various degrees of cross-linking. Suitable collagen sponges can be prepared, for example, analogously to those described for contraceptives in Contraception 15 (1977) 693. Suitable vaginal suppositories can be prepared analogously to known vaginal suppositories used, for example, for the release of other peptide drugs [Insulin (J. Pharm. Pharmacol. 30 (1978) 662, or LH-RH (German Offenlegungsschrift DE-2,836,631)].

Polysiloxane carriers suitable for intrauterine application can be adapted to those polysiloxanes described for example, for the release of prostaglandins in Prostaglandins 12, Suppl. (1976) 1. Furthermore, a collagen depot delivery system for the release of antibiotics is described in the German Offenlegungsschrift DE-3,429,038. This system can also be adapted for interferon delivery.

Slow release formulations and other pharmaceutical formulations of interferons are described in the art or can be prepared analogously to the described formulations.

Utility

The methods provided by the present invention improve embryo survival in mammals, especially in context with oocyte maturation, in vitro fertilization and transfer of embryos. These methods are qualified for reducing the high incidence of embryonic loss and death.

High rates of embryonic loss occur during the time of maternal recognition of pregnancy (e.g. days 12–18 in ewes; days 15–24 in cows), possibly because the embryo does not produce the protein signal early enough or in sufficient quantities. This failure leads to the loss of function of the corpus luteum, a termination of progesterone production and at last to loss of pregnancy.

In the agricultural sector practical implementation is expected to have a positive impact on rate of genetic progress in milk, in meat production, in embryo transfer and in artificial insemination.

The following Experiments and Examples further illustrate the present invention in detail but are not to be construed to limit the scope thereof. The interferon used in the Experiments and Examples was recombinant rBoIFN-alpha₁ produced in accordance with the European patent application EP-0,088,622. This recombinant bovine IFN was supplied lyophilized in a salt mixture that when dissolved at 10 mg/ml, gave a solution of 20 mM succinate buffer, pH 4.5 containing 10.0 mM NaCl, 1.08 mM sodium ethylenediaminetetraacetate, 109.6 mM mannitol and 0.88 mM benzethonium chloride. In addition, a lyophilized carrier solution of the salts without was utilized. Both of these materials were prepared by CIBA-GEIGY, Basle, Switzerland. The stock preparation of IFN had an antiviral titer of $1.4 \times 10^7$ units/mg protein determined by viral plaque inhibition of vesicular stomatitis virus grown on MDBK cells.

Bovine serum albumin (BSA; fraction V, protease free) was from Boehringer Mannheim, (Indianapolis, Ind.).

IFN was dissolved in infusion buffer [10 mM NaPO₄, pH 7.4 containing 0.9% (w/v) NaCl, 100 IU/ml penicillin, 100 $\mu$g/ml streptomycin and 7.5 mg/ml BSA] to a final concentration of 7.5 mg/ml. Solubility of IFN at this concentration was incomplete. Based on determination of protein content of the supernatant fraction using lysozyme as standard [BRADFORD, M. (1976)], 5.2 mg/ml of the IFN was in aqueous form. The entire mixture of IFN was filtered through a 0.45 $\mu$m sterile filter and prepared for infusion. Antiviral activity of the sterilfiltered IFN solution was estimated to be $10^7$–$10^8$ U/ml [FAMILLETTI et al. (1981)], where 1 unit of IFN inhibits 50% of the cytopathic effect of vesicular stomatitis virus on bovine MDBK kidney cells.

Infusion buffer was supplemented with additional BSA to give a final concentration of 15 mg/ml and used as a control infusate. These two infusion solutions (BSA and IFN solutions) were loaded into 0.025 ml artificial insemination straws IMV, Minneapolis, Minn.). For each straw, 100 $\mu$l of the respective solution was aspirated into the middle of the straw. This bolus was lodged between air bubbles. About 50 $\mu$l of infusion buffer without BSA was placed at each end of the straw. The straws were plugged and kept at 4° C. until used (within less than 8 days).

For the intramuscular administration studies, sterile water was added to a 125 mg IFN vial to produce a final concentration of 10 mg/ml or 2.5 mg/ml of IFN in carrier salt solution of 5 mM succinate buffer, pH 4.5 containing 2.5 mM NaCl, 0.27 mM sodium ethylenediaminetetraacetate, 27.4 mM mannitol and 0.22 mM benzethonium chloride. For control injections, either the carrier solution or BSA dissolved in carrier solution to a final concentration of 2.5 mg/ml was used.

EXAMPLE 1

(1a) A pool of 30 non-lactating dairy cows were palpated rectally and ones possessing a functional corpus luteum (CL) were injected with 25 mg of Lutalyse (Upjohn Co., Kalamazoo, Mich.) to regress the corpora lutea. Estrous behavior was checked twice daily and the first 10 cows coming in heat were used for the study. These 10 cows were housed in an outdoor pen and fed corn silage.

The bovine serum albumin (BSA) and IFN solutions were introduced in utero twice daily (8:00 and 20:00 h) from Day 15.5 (evening) through Day 21 (morning) post-oestrus (day of oestrus=day 0). Infusions were by means of an embryo transfer gun (IMV, Minneapolis, Minn.) having two subterminal openings on the plastic sheath. The cow's rectum was emptied and, while the arm of the inseminator was still inside the rectum, the perineal area was washed thoroughly with antibacterial soap, rinsed and dried with a paper towel. The gun covered by the plastic sheath was placed within a rigid protective sheath before being inserted into the vagina. Epidural anesthesia was administered only when it was difficult to pass the gun through the cervix. The solutions were injected into the uterine horn ipsilateral to the CL at a location close to the cranial border of the intercornual ligament. Five cows (1 Holstein, 4 Jersey) were assigned randomly to receive the BSA solution, whereas 5 Jersey cows were assigned randomly to the IFN treatment.

Estrus Detection and Blood Sampling

Estrus behavior was observed twice daily (7:00 and 19:00 h) starting on Day 13 of the estrus cycle. Heat detection was facilitated by the use of KaMar heat mount detection patches (KaMar Incorporated, Steamboat Springs, Colo.) and the presence of an androgenized cow. Serum samples were collected from the coccygeal or jugular vein once daily (7:30 h) beginning on Day 15 and continuing until detection of oestrus to allow determination of circulating progesterone concentrations.

Bacterial Culture and Body Temperature Measurements

Between Day 0–Day 6 following return to estrus after intra-uterine infusion, cows were evaluated for uterine infection. Vaginal mucus on the day of heat was examined carefully for any gross indication of infection. Furthermore, uterine cultures were obtained by the use of Accu-culShure swabs (Accu-Med Corporation, Pleasantville, N.Y.). The swabs were brought to the laboratory in less than 1 h, plated and incubated under aerobic and anaerobic conditions.

To determine whether IFN was pyrogenic, rectal temperatures were measured in all cows on one day of the trial at 0, 0.5, 1, 3 and 5.5 h after uterine infusion of IFN and BSA.

Progesterone Determinations

Progesterone was measured in duplicate from serum samples using an enzyme-linked immunosorbent assay (ELISA, Enzygnost, Hoechst-Roussel Agri-Vet, Somerville, N.J.) read in an automated microtiter spectrophotometer. There was parallelism between the inhibition of binding of conjugated progesterone to antibody-coated wells achieved by various dilutions of a pregnant cow serum pool to the inhibition achieved by standards. The intra- and inter-assay coefficients of variation for four assays were 8.8% and 13.9%, respectively. Limit of detection of the assay (90% of maximal binding) was 0.5 ng/ml.

Effects of Intrauterine Infusions on Interestrous Interval

Intrauterine administration of IFN to cyclic cows from Day 15.5 through 21 extended (P<0.02) the length of the oestrus cycle as compared to cows receiving BSA [26.8±1.39 vs 22.8±80 d (FIG. 1)]. Of the five cows receiving IFN, four had extended cycles of 26 to 30 days. The remaining cow from the IFN treatment group (oestrous cycle length=22 d) was the most difficult of the animals to achieve trans-cervical passage of the embryo transfer gun and the only one needing extensive epidural anesthesia during the trial (4 times).

Effects of Intrauterine Infusions on Serum Progesterone

Figure 2A:
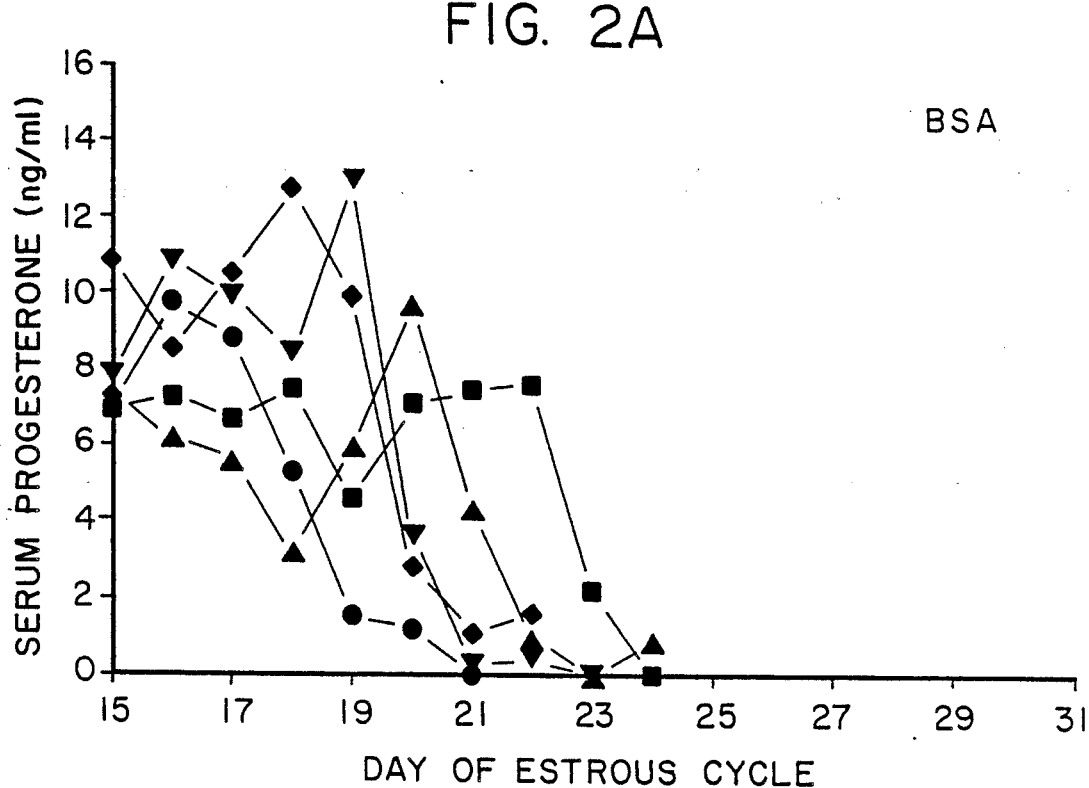
FIG. 2 shows the effect of intrauterine administration of bovine serum albumin (panel A) and interferon (panel B) from Day 15.5 to 21 after estrus on circulating serum progesterone concentrations. Plotted are individual profiles from each cow in the experiment. Note that the decline in progesterone concentrations was delayed in the IFN-treated cows ($P<0.02$), indicating that the lifespan of the corpus luteum was extended by IFN.
Figure 2B:
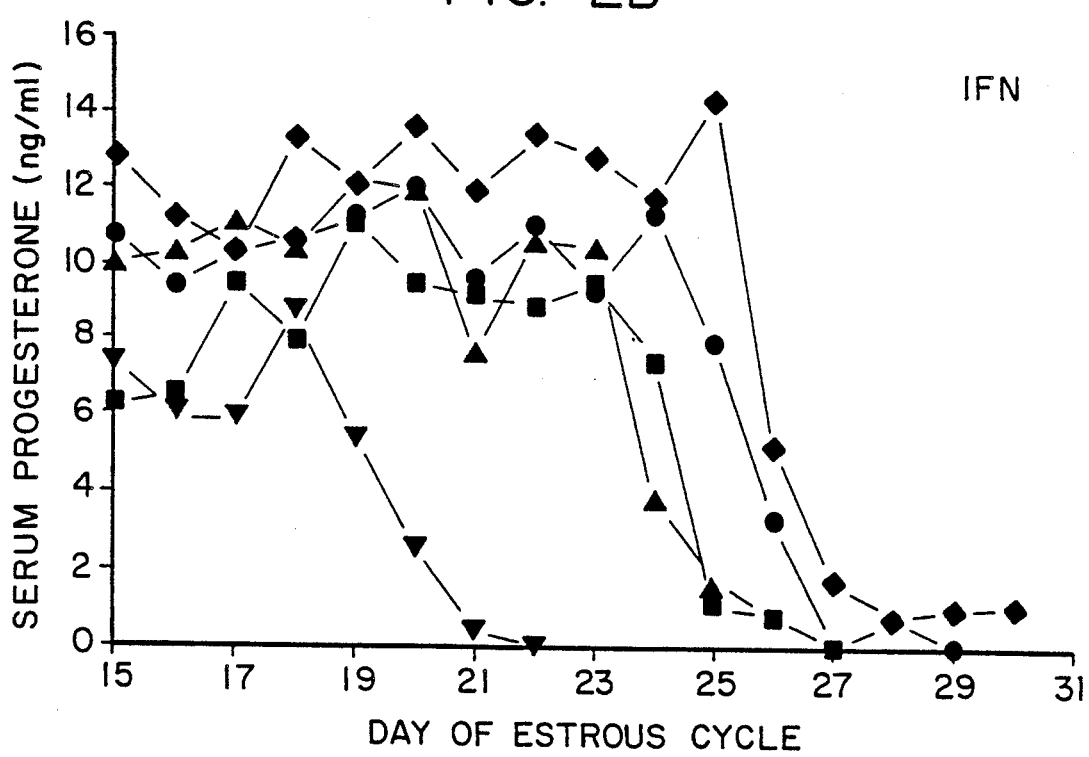

Functional lifespan of the CL was estimated as the interval between previous estrus and the day when progesterone first dropped below 1.5 ng/ml (FIG. 2). Based on this criterion, IFN extended the functional lifespan of the CL (P<0.02), with intervals being 25.6±1.21 for IFN-treated cows and 22±0.71 d for the BSA-treated cows.

Effects of Intrauterine Infusions on Body Temperature and Uterine Infection

Neither BSA or IFN administration altered body temperature, which remained between 38.4 and 39.2 during the 5.5 h examination period after infusion. Based on cultures of uterine swabbing obtained after the experiment, no animals exhibited uteri with bacterial contamination.

(1b) Example (1a) was repeated under the following modified conditions:

Fifteen lactating dairy cows maintained in an outdoor lot were palpated rectally and those possessing a functional corpus luteum (CL) were injected with 25 mg of Lutalyse (Upjohn Co., Kalamazoo, Mich.) to regress corpora lutea. Cows were checked twice daily for estrus. The first 10 cows (6 Holstein and 4 Jersey) exhibiting estrus were assigned randomly to receive control (1.5 mg BSA/infusion; 5 cows) or IFN solutions (1.0 mg IFN with 0.5 mg of BSA/infusion; 5 cows). The control and IFN solutions were introduced in utero, twice daily (6:00 h and 18:00 h) from Day 14 (morning) through Day 21 (evening) after estrus (day of estrus=Day 0). The infusions technique was used described previously except that no epidural anesthesia was given.

Estrous Detection and Blood Sampling

The animals were observed twice daily (7:00 and 19.00 h) for returns to estrus starting on Day 13 of the estrous cycle. Estrous detection was facilitated by the use of heat detectors (KaMar) for dairy cows. In both experiments, blood samples were collected from the coccygeal vein in a vacutainer tube (Becton Dickinson and Company, Rutherford, N.J.) once daily (between 6:00 and 9:30 h) beginning on Day 14 of the estrous cycle and continuing until detection of estrus. Blood was allowed to clot at room temperature for 2-3 h and stored an additional 2-6 h at 4° C. The serum was harvested by centrifugation for 10 min at 500×g and was then frozen and maintained at −20° C. unitl assayed.

Progesterone Determination

The concentrations of progesterone in serum were measured in duplicate, using 100 or 200 μl of samples, in a radioimmunoassay as described by Knickerbocker and coworkers (1986). The intra- and interassay coefficients of variation for four assays were 7.0 and 9.0% respectively. Sensitivity of the assay was 31.2 pg/tube.

Results

Figure 4:
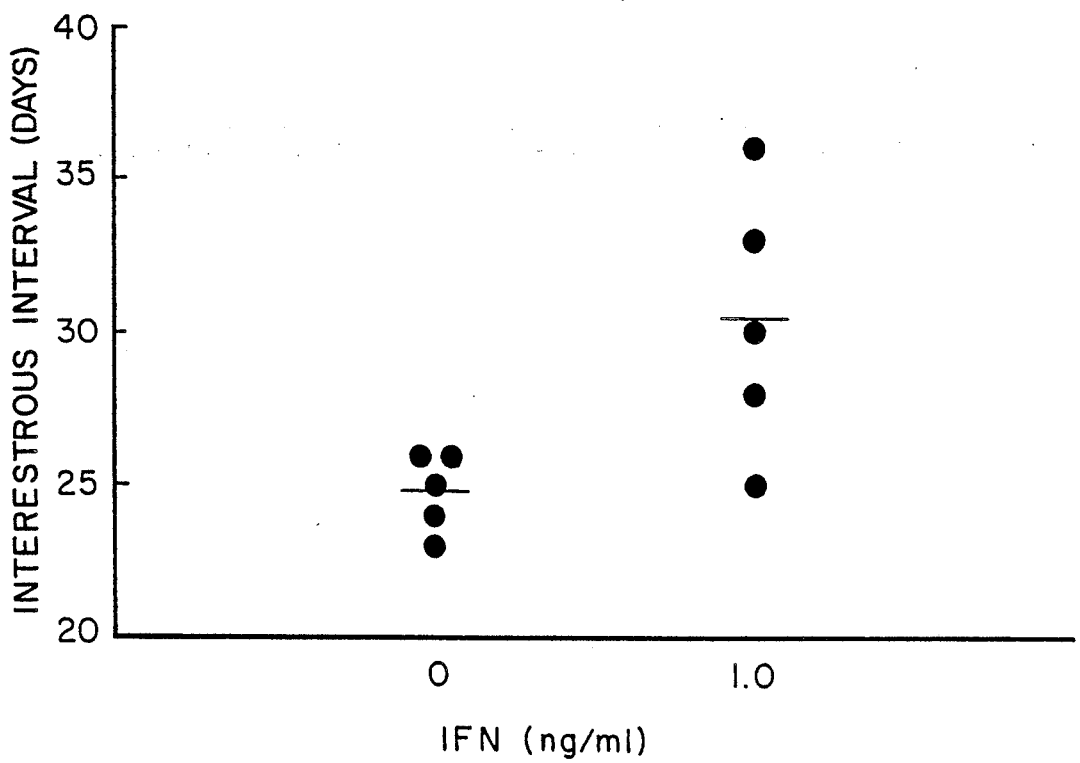
FIG. 4 shows the effects of intrauterine infusion of rBoIFN$\alpha_I$1 to lactating dairy cows. Cows receiving rBoIFN$\alpha_I$1 in utero had estrous cycles of 25 to 36 days in length. All but one of five cows had cycle lengths greater than 27 days. The control cows returned to estrus within 24 to 26 days after estrus. This difference is significant ($p<0.02$).

Effects of intrauterine infusion of IFN on interestrous interval and corpus luteum lifespan Lactating dairy cows receiving IFN in utero had estrous cycles of 25 to 36 days in length (FIG. 4). All but one of five cows had cycle lengths greater than 27 days. In contrast, all the control cows returned to estrus within 24 to 26 days after estrus. Overall, the mean interestrous interval was prolonged ($P<0.02$) in the IFN-treated group compared to the control group ($30.4\pm1.91$ vs $24.8\pm0.58$ d). IFN also extended ($P<0.03$) the functional lifespan of the CL ($28.4\pm2.01$ d for IFN-treated cows vs $23.6\pm0.75$ d for control cows).

EXAMPLE 2

Parenteral Administration of Interferon

A pool of 25 dairy Simmental heifers, 18–20 months old weighing 350–420 kg were synchronized using prostaglandin analogues (Estrumate ® COOPERS Animal Health). The first ten heifers showing signs of estrus were selected for the study. These animals were housed in an indoor pen and fed corn silage and hay.

INTERFERON

Recombinant bovine interferon alpha (rBoIFN$\alpha_1$I) was produced in *E. coli* by recombinant DNA technology and purified to homogeneity as determined by high performance liquid chromatography and SDS polyacrylamide gel electrophoresis. The stock preparation has an antiviral titer of $1.4\times10^7$ units/mg protein determined by viral plaque inhibition of vesicular stomatitis virus grown in MDBK cells.

STUDY DESIGN

Each test animal (5) received 20 mg in 2 ml of rBoIFN$\alpha_1$I intramuscularly (IM) twice a day from day 15 to day 19 post estrus (7:00 and 16:00). Control animals (5) received an equivalent volume (2 ml) of placebo.

Blood samples were taken daily (8:00) by venepuncture from day 15 through day 26 post estrus and plasma separated.

Rectal temperatures were also measured daily (day 15-21).

Estrous behaviour was observed for at least 5 minutes four times a day (7:00, 12:00, 16:00, 19:00) starting on day 15 of the estrus cycle. The heifers standing to be mounted by other heifers that did not try to avoid or escape were considered to be on heat. Vaginal mucus on the day of heat was also observed carefully.

The trial was performed blind where personnel involved in estrus detection and progesterone assay were unaware of the treatment administered.

PROGESTERONE DETERMINATION

Progesterone was measured from plasma samples using an enzyme linked immunosorbent assay (commercial ELISA kit from Cambridge Veterinary Science [Cambridge UK]). Detection limit of the assay was 0.5 mg/ml.

STATISTICAL ANALYSIS

Treatment effects were analyzed using a student t-test.

TEST RESULTS

Body temperature

No significant differences between IFN and placebo treated animals were observed during the first seven days of the study (see Table I below).

TABLE I

Effect of intramuscular injection of rBoIFN$\alpha_1$I (20 mg twice daily) on body temperatures of heifers (°C.).

| Days post estrus | IFN treated heifers | Placebo treated heifers |
|---|---|---|
| 15 | $38.8 \pm 0.3$ | $38.8 \pm 0.3$ |
| 16 | $39.0 \pm 0.6$ | $38.4 \pm 0.24$ |
| 17 | $38.8 \pm 0.8$ | $38.3 \pm 0.2$ |
| 18 | $38.5 \pm 0.6$ | $38.3 \pm 0.14$ |
| 19 | $38.9 \pm 0.7$ | $38.3 \pm 0.3$ |
| 20 | $38.7 \pm 0.3$ | $38.4 \pm 0.16$ |
| 21 | $38.5 \pm 0.4$ | $38.7 \pm 0.26$ |

Effect on interestrous interval

Figure 3:
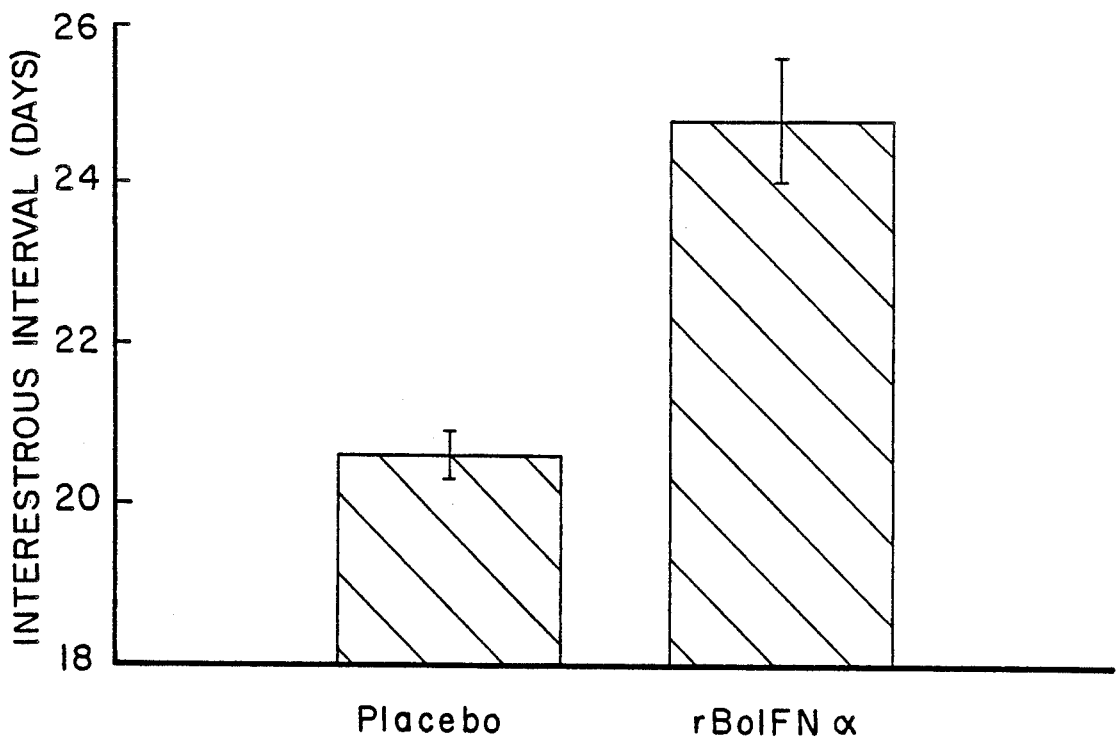
FIG. 3 shows the effect of intramuscular administration of rBoIFN$\alpha_I$1 from day 15 to 19 postestrus on the interestrous interval. The mean interestrous interval for IFN treated heifers ($24.6 \pm 1.35$) was greater than for placebo treated heifers ($20.6 \pm 0.5$).

Intramuscular administration of IFN to cyclic heifers from day 15 to day 19 postestrus significantly extended ($p<0.01$) the length of the estrous cycle (FIG. 3). All the placebo treated animals came on heat on day 20 and 21. Only one heifer of the IFN treated group came on heat on day 23, the others on day 24, 25 and 27 respectively.

Progesterone levels

In the rBoIFN$\alpha_1$I treated heifers luteal function was maintained significantly longer than the control heifers as shown by progesterone levels on day 22 post estrus.

TABLE II

| Progesterone Levels | Placebo | IFN α treated |
|---|---|---|
| >10 ng | 0 | 4 |
| intermediate | 1 | 1 |
| <3 ng | 4 | 0 |

Table II shows the effect of intramuscular administration of rBoIFN$\alpha_1$I from day 15 to 19 after estrus on plasma progesterone concentrations on day 22.

EXAMPLE 3

Parenteral Administration of Interferon

Fifty dairy heifers, weighing from 230 to 343 kg and kept in four different outdoor pens, were rectally palpated and those possessing a functional CL injected with 18.5 mg of Lutalyse (Upjohn Co., Kalamazoo, Mich.). Estrous behavior was checked three times daily (7:00, 1:00, 19:00 h) and those detected in estrus were assigned randolmy within pens to one of four doses of recombinant bovine IFN alpha in accordance with Example 2 (0, 2.5, 5.0, 10.0 mg/injection). Animals receiving 0 mg IFN received a control injection of 4 ml of BSA (2.5 mg/ml) dissolved in neutral carrier solution. Injections were given intramuscularly twice daily (7:00, 19:00 h) from Day 14 to 21 of the estrous cycle. The experiment was performed on two different occasions, using different heifers, so as to obtain the necessary numbers of animals per group (N=6, 5, 5, and 7 for 0, 2.5, 5.0 and 10.0 mg, respectively). Therefore, the statistical analysis included effects of period.

Estrus Detection and Blood Sampling

The test animals were observed twice daily (7:00 and 19:00 h) for returns to estrus starting on Day 13 of the estrous cycle. Estrous detection was facilitated by the use of heat detectors (KaMar) for dairy cows. In both experiments, blood samples were collected from the coccygeal vein in a vacutainer tube (Becton Dickinson and Company, Rutherford, N.J.) once daily (between 6:00 and 9:30 h) beginning on Day 14 of the estrous cycle and continuing until detection of estrus. Blood was allowed to clot at room temperature for 2-3 h and stored an additional 2-6 h at 4° C. The serum was harvested by centrifugation for 10 min at 500×g and was then frozen and maintained at −20° C. until assayed.

Blood samples were taken daily (8:00 h) by jugular venipuncture from Day 15.26 after estrus into heparinized tubes. Plasma was harvested by centrifugation and then frozen and maintained at −20° C. until assayed.

Progesterone Determination

The concentrations of progesterone in serum were measured in duplicate, using 100 or 200 μl of samples, in a radioimmunoassay as described by Knickerbocker and coworkers (1986). The instra- and interassay coefficients of variation for four assays were 7.0 and 9.0% respectively. Sensitivity of the assay was 31.2 pg/tube.

TEST RESULTS

Figure 5:
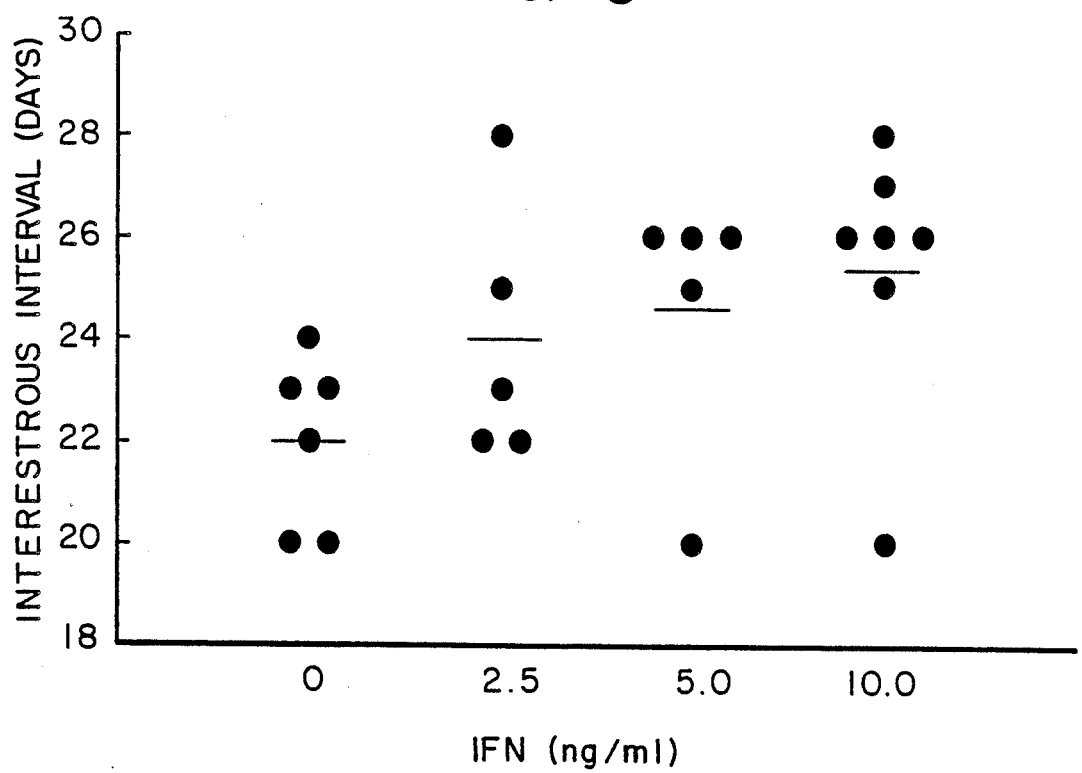
FIG. 5 shows the effects of intramuscular administration of rBoIFN$\alpha_I$1 on interestrous interval. The six heifers receiving 0 mg of IFN had an interestrous interval between 20 and 24 days in length, whereas groups receiving 2.5, 5.0 and 10 mg/injection included several heirers with prolonged estrous cycles (2/5, 5/6 and 6/7 heifers with a cycle length greater than 24 days; difference significant at $p<0.02$).

Effects of intramuscular administration of IFN on interestrous and corpus luteum lifespan The six heifers receiving 0 mg of IFN had an interestrous interval between 20 to 24 days length, whereas groups receiving 2.5, 5.0 and 10.0 mg/injection included several heifers with prolonged estrus cycles (2/5, 5/6 and 6/7 heifers with a cycle length greater than 24 days; FIG. 5). The mean interestrous intervals were 22.0±0.68, 24.0±1.14, 24.6±1.17 and 25.4±0.97 d, respectively for heifers receiving 0, 2.5, 5.0 and 10.0 mg of IFN. Orthogonal contrasts revealed that IFN-treated heifers had prolonged cycles (P<0.02) when compared to the control group. Cycle lengths did not differ between the 2.5, 5.0 and 10 mg/injection groups. Nonetheless, the estrous cycle length increased slightly as dose of IFN increased. However, when the results were analyzed as categorical data, orthogonal contrasts confirmed dose-dependent effects of IFN. The number of animals in the IFN treated groups (2.5 and 10 mg) showing a prolonged cycle was significantly higher (P<0.04) when compared to the control group. The 5.0 and 10.0 mg-treated groups also contained more animals with an extended interestrous interval than the 2.5 mg treated group (P<0.10). There was no difference between groups treated with 5.0 and 10.0 mg. Means for the period of functional lifespan on the corpus luteum were 20.5±0.56, 23.0±1.26, 23.6±1.17 and 24.1±074 respectively for the 0, 2.5, 5.0, and 10.0 mg treated groups. Using orthogonal contrasts, luteal lifespan was longer (P<0.01) in the IFN-treated groups as compared to the control group and there were no significant differences between groups treated with 2.5, 5.0 and 10 mg.

Thus, a preferred embodiment of the present invention is the systemic administration, preferably the intramuscular administration, of an interferon alpha to mammals to maintain the function of the CL during early pregnancy in order to increase the mammalian fertility.

EXAMPLE 4

Improvement of fertility in heifers 22 healthy Simmental heifers, 18-20 months of age, of various origin, weighing approximately 300-400 kg that were cyclic and non pregnant were used. All animals were dehorned prior to beginning of the study. Each animal was individually identified by a numbered ear tag. The animals were synchronized according to Example 2 and kept in farm pens in an open yard shed. 11 target animals (treated with rBoIFNα) in one pen and the control group of 11 animals (treated with placebo) in the other pen. Treatment, insemination and estrous detection were carried out according to the following schedule:

TEST SYSTEM 2 treatment groups (A) and (B).

Group (A) treated with placebo (11 heifers). Placebo=sterile double distelled water.

Group (B) treated with rBoIFNα (11 heifers). rBoIFNα was administered intramuscularly twice a day (10+10 mg/kg) from day 15 to 19 postestrous.

The test IFN was lyophilized powder of rBoIFNαl dissolved in sterile water for injection USP. with a final concentration of 2.5 mg/ml.

Estrous (heat) detection, blood sampling and progesterone determination as described in Example 1.

TEST PLAN

March 2 Synchronisation
March 13 Synchronisation
March 16 Artificial insemination ($J_0$)
March 31 IFN treatment ($J_{15}$)

| April 1 | IFN treatment | | |
| April 5 | : | Blood samples | |
| April 6 | : | : | Estrus detection |
| April 7 | : | : | : |
| April 13 | : | : | : |

The efficiency of rBoIFNαl is determined by comparing the fertility rate of both groups (A) and (B) as shown in the following table:

| | TEST RESULTS | |
|---|---|---|
| | Group (A) 11 heifers treated with placebo | Group (B) 11 heifers treated with IFN |
| day 28 (detection of estrous and progesterone level) | 3 | 8 |
| day 60 (pregnancy diagnosis by rectal palpation) | 3 | 6 |
| day 90 (rectal palpation) | 0 | 4 |
| calving | 0 | 4 |

Thus, heifers treated with IFN showed a significant improvement of fertility.

DISCUSSION

From the data presented, it is evident that local or systemic administration of interferon alpha ($IFN_\alpha$) can regulate functional lifespan of the corpus luteum (CL) and length of estrous cycle. Intrauterine infusion of IFN$_\alpha$ prolonged the interestrous interval to an average of 30.4 days, an extension similar to what was reported by Knickerbocker and coworkers (1986) using in utero infusions of proteins from conceptus-conditioned culture medium from D 15.5 through 21 after estrus. Cows receiving an intrauterine infusion of BSA also had slightly extended interestrous intervals, possibly due to uterine irritation.

Of particular importance to the present invention is the finding that systemic administration of IFN$_{60}$ by an intramuscular route also prolongs interestrous interval and the functional lifespan of the CL. In two separate studies administration of IFN via intramuscular injection extended estrous cycle length by an average of 2 to 4 days. It thus is evident that IFN$_{60}$ can be given to mammals to regulate luteal function trough systemic routes that are easy to access. Therefore, systemic administration of IFN$_\alpha$ also has the potential of increasing fertility through its actions on blocking luteolysis.

EXAMPLE 5

Interferon Formulations

|     | Ingredient | % by weight |
| --- | --- | --- |
| (a) | rBoIFN$\alpha_j$1 | $1 \times 10^7$ IU/100 g product |
|     | glycerin | 15 |
|     | sodium carboxy-methyl cellulose | 2 |
|     | sodium lauryl sulfate | 0.3 |
|     | distilled water | up to 100 |
| (b) | rBoIFN$\alpha_j$1 | $1 \times 10^6$ IU/100 g product |
|     | glycerin | 30 |
|     | glucuronic acid | 1 |
|     | white petrolactum | 25 |
|     | stearyl alcohol | 22 |
|     | citrat buffer (pH 4.5, 0.1 mole/liter distilled water) | up to 100 |

References

BAZER, F. and FIRST, M. 1983 J. Anim. Sci 57 suppl: 425

GODKIN, J. et al. 1982 J. Reprod. Fertil. 65: 141

GODKIN J., BASER, F. and ROBERTS, R. 1984 Endocrinology 114: 120

GODKIN J. et al. 1984 J. Reprod. Fertil. 71: 57

HELMER, S. D. et al. 1987 J. Reprod. Fertil. 79: 83

HANSEN, P. et al. 1985 Endocrinology 117: 1424

IMIKAWA, K. et al. 1987 Nature 330: 337

MARTAL, J. et al. 1979 J. Reprod. Fertil. 56: 63

ROWSON, L. and MOOR, R. 1967 J. Reprod. Fertil. 113: 511

SHORT, 1969 in Foetal Autonomy (Wolstenholme, C. and O'Connor, M. eds), Churchill London 2-26

STEWART, H. et al. 1987 J. Endocrinology, 115 R 13-R 15.

Knickerbocker, J. J., et al. 1986 J. Reprod. Fertil. 77: 381.

BRADFORD, M. 1976 Anal Biochem 72:248.

FAMILLETTI, P. C. et al. 1981 Methods Enzymol 78:387.

ANTHONY, R. N. et al. 1988 Endocrinology 123:1274.

HELMER, S. D. et al. 1988 Mol. Cell Endocrinology 58:103.

THATCHER et al. 1988 J. Reprod. Fertil. Suppl. 37: in press.

What is claimed is:

1. A method for enhancing fertility in a female mammal comprising administering to said mammal an effective mammalian fertility enhancing amount of an interferon alpha together with one or more pharmaceutically acceptable adjuncts or excipients.

2. A method according to claim 1 wherein the mammal is in need of an enhanced fertility.

3. A method according to claim 1 wherein the interferon alpha is of heterologous origin.

4. A method according to claim 1 wherein the interferon alpha is of homologous origin.

5. A method according to claim 1 wherein the interferon is an alpha II type interferon.

6. A method according to claim 1 wherein the interferon is an alpha I type interferon.

7. A method according to claim 1 wherein the interferon is an animal interferon alpha.

8. A method according to claim 1 wherein the interferon is a human interferon alpha.

9. A method according to claim 7 wherein the animal interferon is bovine, ovine or porcine interferon alpha.

10. A method according to claim 8 wherein the human interferon is human alpha I or human alpha II interferon.

11. A method according to claim 9 wherein the animal interferon is bovine alphaI or bovine alphaII interferon.

12. A method according to claim 11 wherein the bovine interferon is rbovine interferon-alpha$_j$1 (rBoIFN$\alpha_j$1).

13. A method according to claim 1 wherein the mammal is a woman.

14. A method according to claim 1 wherein the mammal is a domestic animal.

15. A method according to claim 14 wherein the mammal is a farm animal.

16. A method according to claim 1 wherein the interferon alpha is an interferon produced by means of recombinant DNA technology.

17. A method according to claim 1 wherein the interferon alpha is administered parenterally in a daily dosage of 0.1 to 100 mg/animal.

18. A method according to claim 17 wherein the interferon alpha is administered parenterally in a daily dosage of 0.5 to 50 mg/animal.

19. A method according to claim 1 wherein the interferon alpha is administered into the uterus in a daily dosage of 0.1 to 10 mg/animal.

20. A method according to claim 19 wherein the interferon alpha is administered into the uterus in a daily dosage of 0.5 to 5 mg/animal.

21. A method according to claim 1 wherein the interferon alpha is administered intravaginally.

22. A method according to claim 21 wherein the interferon alpha is administered by means of an intravaginal sponge.

23. A method of prolonging the lifespan of the corpus luteum in a mammal comprising administering an effective corpus luteum lifespan prolonging amount of an interferon alpha together with one or more pharmaceutically acceptable adjuncts or excipients.

24. A method according to claim 23 wherein the mammal is in need of a prolonged lifespan of the corpus luteum.

25. A method according to claim 23 wherein the interferon alpha is of heterologous origin.

26. A method according to claim 23 wherein the interferon alpha is of homologous origin.

27. A method according to claim 23 wherein the interferon is an alpha II type interferon.

28. A method according to claim 23 wherein the interferon is an alpha I type interferon.

29. A method according to claim 23 wherein the interferon is an animal interferon alpha.

30. A method according to claim 23 wherein the interferon is a human interferon alpha.

31. A method according to claim 29 wherein the animal interferon is bovine, ovine or porcine interferon alpha.

32. A method according to claim 30 wherein the human interferon is human alpha I or human alpha II interferon.

33. A method according to claim 31 wherein the animal interferon is bovine alpha I or bovine alpha II interferon.

34. A method according to claim 30 wherein the bovine interferon is rbovine interferon-alpha$_I$1 (rBoIF-N$\alpha_I$1).

35. A method according claim 23 wherein the mammal is a woman.

36. A method according to claim 23 wherein the mammal is a domestic animal.

37. A method according to claim 36 wherein the mammal is a farm animal.

38. A method according to claim 23 wherein the interferon alpha is an interferon produced by means of recombinant DNA technology.

39. A method according to claim 23 wherein the interferon alpha is administered parenterally in a daily dosage of 0.1 to 100 mg/animal.

40. A method according to claim 39 wherein the interferon alpha is administered parenterally in a daily dosage of 0.5 to 50 mg/animal.

41. A method according to claim 23 wherein the interferon alpha is administered into the uterus in a daily dosage of 0.1 to 10 mg/animal.

42. A method according to claim 41 wherein the interferon alpha is administered into the uterus in a daily dosage of 0.5 to 5 mg/animal.

43. A method according to claim 23 wherein the interferon alpha is administered intravaginally.

44. A method according to claim 43 wherein the interferon alpha is administered by means of an intravaginal sponge.

45. A method according to claim 1 wherein the interferon alpha is administered in form of a slow release formulation.

46. A method according to claim 23 wherein the interferon alpha is administered in form of a slow release formulation.

* * * * *

UNITED STATES PATENT AND TRADEMARK OFFICE
CERTIFICATE OF CORRECTION

PATENT NO. : 4,997,646
DATED : March 5, 1992
INVENTOR(S) : Peter J. Hansen et al.

It is certified that error appears in the above-identified patent and that said Letters Patent is hereby corrected as shown below:

In column 1, following the title but before "This is a continuation-in-part...", insert the following:

-- This invention was made with government support awarded by the National Institute of Health. The government has certain rights in the invention.

CROSS REFERENCE TO RELATED APPLICATION --.

Signed and Sealed this

Twenty-eighth Day of September, 1993

Attest:

Attesting Officer

BRUCE LEHMAN

Commissioner of Patents and Trademarks